United States Patent
Joo et al.

(10) Patent No.: US 9,255,694 B2
(45) Date of Patent: Feb. 9, 2016

(54) REFLECTOR STRUCTURE OF ILLUMINATION OPTIC SYSTEM

(71) Applicant: Samsung Electronics Co., Ltd., Suwon-Si, Gyeonggi-Do (KR)

(72) Inventors: Won-Don Joo, Incheon (KR); Woo-Seok Ko, Seoul (KR); Yu-Sin Yang, Seoul (KR); Sue-Jin Cho, Yongin-si (KR); Sang Don Jang, Suwon-si (KR); Byeong Hwan Jeon, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 351 days.

(21) Appl. No.: 13/762,782

(22) Filed: Feb. 8, 2013

(65) Prior Publication Data
US 2013/0208486 A1 Aug. 15, 2013

(30) Foreign Application Priority Data
Feb. 10, 2012 (KR) ........................ 10-2012-0013512

(51) Int. Cl.
*F21V 13/04* (2006.01)
*G01N 21/88* (2006.01)
*G01N 21/95* (2006.01)

(52) U.S. Cl.
CPC ............ *F21V 13/04* (2013.01); *G01N 21/8806* (2013.01); *G01N 21/9501* (2013.01); *G03B 2215/0582* (2013.01); *G03B 2215/0592* (2013.01)

(58) Field of Classification Search
CPC ............... F21V 13/04; G01N 21/8806; G01N 21/9501; G03B 2215/0582; G03B 2215/0592
USPC .................................. 362/560, 581
See application file for complete search history.

(56) References Cited

U.S. PATENT DOCUMENTS 6,953,252 B2 * 10/2005 Way .............................. 362/297
7,178,948 B2 * 2/2007 Gupta .................. G02B 6/0031
359/853

* cited by examiner

*Primary Examiner* — Stephen F Husar
(74) *Attorney, Agent, or Firm* — Harness, Dickey & Pierce

(57) ABSTRACT

An illumination optic system includes a convex mirror to reflect light from a light source to towards a lens. The light source is at a first focus position and the lens is at a second focus position of the mirror. The system also includes a reflector to reflect light not incident on the lens toward the convex mirror. The reflector has a light guide hole to guide light to the incidence surface of the lens.

14 Claims, 5 Drawing Sheets

REFLECTOR STRUCTURE OF ILLUMINATION OPTIC SYSTEM

CROSS-REFERENCE TO RELATED APPLICATION

This application claims the benefit of Korean Patent Application No. 2012-0013512, filed on Feb. 10, 2012 in the Korean Intellectual Property Office, the disclosure of which is incorporated herein by reference in its entirety.

BACKGROUND

1. Field

The present disclosure relates to emission of light.

2. Description of the Related Art

A surface inspection apparatus is used to inspect various objects including semiconductor wafers and display panels. In one type of surface inspection apparatus, uniform and parallel light is radiated at a semiconductor wafer or display panel to obtain an image that may be visually inspected for defects or other details. The illumination optic system may also be used to form a desired pattern on a substrate during, for example, semiconductor device manufacturing.

Illumination optic systems of the aforementioned and other types fail to provide light at a desired level and/or fail to provide a sufficient degree of uniformity of light for various applications. Also, a significant amount of light may be lost or otherwise dissipated, which results in inspection or pattern failures.

SUMMARY

One or more embodiments provide an illumination optic system for reducing loss of light emitted from an illumination optic system.

In accordance with one embodiment, an illumination optic system includes a light source, an oval shape reflection mirror, a lens, and a reflector. The oval shape reflection mirror may be configured to have a light source positioned at a first focus, and allow light radiated from the light source to be reflected so that the reflected light is focused on a second focus. The lens may be configured to have an incidence surface thereof positioned on the second focus of the oval shape reflection mirror. The reflector may be provided with a reflection surface and a light guide hole. The reflection surface may be configured to reflect light, which is not incident onto the lens among the light reflected by the oval shape reflection mirror, toward the oval shape reflection mirror so that the light is reflected again by the oval shape reflection mirror. The light guide hole may be configured to guide the light, which is reflected again, to the incidence surface of the lens.

The lens may be coupled to the reflector in a way that the incidence surface of the lens is inserted into the light guide hole while forming a gap between the incidence surface of the lens and the light guide hole of the reflector. The light guide hole may have a diameter larger than a diameter of the incidence surface of the lens to secure the gap.

The reflector and the lens may be disposed so that the reflection surface of the reflector is coplanar with the incidence surface of the lens. Also, the reflector and the lens may be disposed so that the reflection surface of the reflector is positioned ahead of the incidence surface of the lens in a light axis, wherein an inner surface of the light guide hole of the reflector is coated with reflection material to form a reflection coating surface.

The reflector and the lens may be disposed so that a rear surface of the reflector is coplanar with the incidence surface of the lens. The reflector may be at least one of a mirror, a retro-reflector and a retro-reflector array. The lens may be one of a rod lens and a fly-eye lens.

In accordance with another embodiment, an illumination optic system comprises a light source; a first reflector coupled the light source; a lens in front of the light source and first reflector; and a second reflector adjacent the lens and configured to reflect light toward the first reflector. The first reflector is configured to reflect the light reflected from the second reflector towards the lens, and the second reflector is spaced from the lens to allow a first portion of the light reflected from the second reflector to pass through the space and a second portion of the light reflected from the second reflector to change direction to pass into the lens.

The first reflector may be an oval-shaped mirror. The light source may be located at a first focal position of the mirror, and an incident surface of the lens may be located at a second focal position of the mirror.

The space may be filled with a medium having a different index of refraction than the lens. The medium may be air.

The second reflector may include a light guide hole and the lens may be adjacent the light guide hole. The light guide hole may have a first size, and the incident surface of the lens may have a second size less than the first size. A size of the space may be based on a difference between the first size and the second size.

A reflection surface of the second reflector may be substantially coplanar with an incident surface of the lens. Or, a rear surface of the second reflector may be substantially coplanar with an incident surface of the lens.

The second reflector may include a retro-reflector and a retro-reflector array, and the lens may be a rod lens or a fly-eye lens.

Additionally, a reflective coating may be coupled to the second reflector, wherein the reflective coating is at a position to reflect light from the light source and first reflector into the lens. The reflective coating may be coupled to a surface of the second reflector that crosses a central optical axis of the lens.

In accordance with another embodiment, an illumination optic system comprises a light source; a first reflector coupled the light source; a lens in front of the light source and first reflector; a second reflector between the light source and lens, and a third reflector adjacent the lens, the second reflector to reflect light toward the first reflector. The first reflector is configured to reflect light reflected from the second reflector towards the lens, and the third reflector is configured to reflect light from the light source and first reflector into the lens.

The third reflector may be a reflective coating. The third reflector may be coupled to a surface of the second reflector that faces a direction that crosses a central axis of the lens. The third reflector may contact the second reflector and the lens. And, the third reflector may not overlap an incident surface of the lens.

The second reflector may include a hole, and the third reflector may overlap the hole in the second reflector. Also, an incident surface of the lens may be in a first plane, and a surface of the second reflector may be in a second plane different from the first plane.

In accordance with one or more embodiments, loss of light from the illumination optic system may be reduced after the light is radiated from a light source. By preventing this light loss, an increased amount of light may be generated for various applications including but not limited to inspection of test objects and the projection of patterns on wafers during semiconductor device manufacturing. As a result, flexibility of design of the illumination optics may be realized and a higher quality of illumination optic system may be provided.

BRIEF DESCRIPTION OF THE DRAWINGS

The above and other features and advantages of example embodiments will become more apparent by describing in detail example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION OF EXAMPLE EMBODIMENTS

Figure 1:
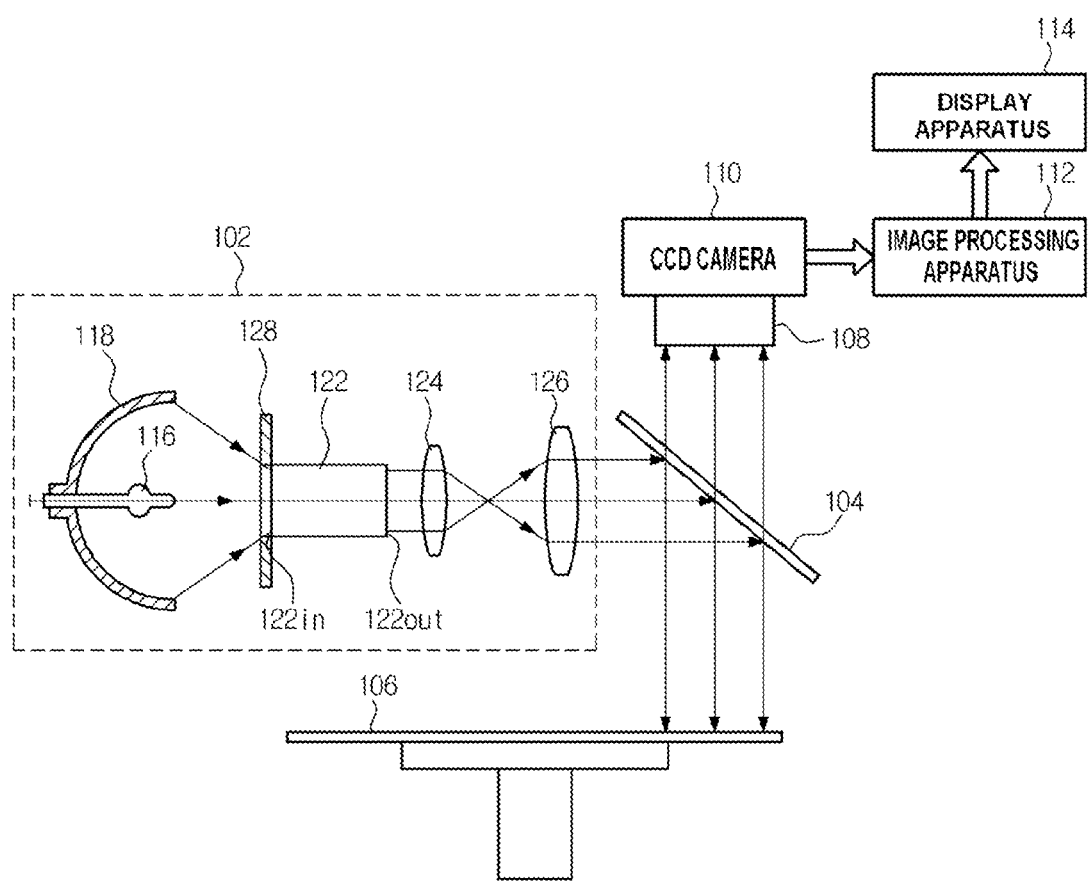
FIG. 1 shows one embodiment of an illumination optic system.

Detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it may be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (eg., "between" versus "directly between", "adjacent" versus "directly adjacent", etc.).

The terminology used herein is for the purpose of describing particular embodiments only and is not intended to be limiting of example embodiments. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

FIG. 1 shows one embodiment of an illumination optic system 102 which generates and directs parallel light onto a half mirror 104. The half mirror 104 reflects a particular wavelength or band of wavelengths of the received light onto the surface of a wafer 106. The light reflected at the surface of the wafer 106 passes through half mirror 104 and falls incident on an imaging optical system 108.

The imaging optical system 108 forms an image based on the light reflected from wafer 106 through the half mirror 104. A charge coupled device (CCD) camera 110 photographs the image and generates an image signal.

An image processing apparatus 112 processes the image signal generated by the CCD camera 110 to generate image data.

A display apparatus 114 displays an image based on the image data. By viewing the image displayed at the display apparatus 114, the status of a surface of the wafer 106 may be visually inspected. In order to precisely inspect the status of the surface of the wafer 106, the surface of the wafer 106 is to be illuminated with sufficient amount of parallel light.

In accordance with one embodiment, the illumination optic system 102 includes a lamp 116 to radiate light is installed as a light source at a position of a first focus of convex reflection mirror 118. The convex reflection mirror 118 guides (e.g., focuses) the light from lamp 116 along a desired path.

In accordance with one embodiment, the convex reflection mirror 118 may corresponds to a portion of an oval having two focal positions. The reflection mirror 118 may be configured to set the position of the lamp 116 at a first focus position and lens 122 (discussed in greater detail below) may be located at a second focus position.

One or more lenses or optical elements may be included along the light path between mirror 118 and half mirror 104. In accordance with one example arrangement, these lenses or optical elements include a lens group that includes a rod lens 122, a focus lens 124, and a collimation lens 126 arranged in series. Hereinafter, mirror 118 may be referred to as an oval shaped mirror for illustrative purposes, with the understanding that mirror 118 may alternatively having another convex or curved shape.

The rod lens 122 converts incident light from mirror 118 into uniform light. The rod lens 122 may be formed of glass or another transparent material and may have a shape of a tube having a polygonal or other cross section. An incident surface of lens 122in and a surface from which the converted light exits lens 122 may be perpendicular to a light axis which, for example, may pass through source 116 or another optical feature of the system. The incident surface of rod lens 122 may be located at second focus position of oval shape reflection mirror 118. Instead of rod lens 122, a fly-eye lens or another type of optical element may be used.

The focus lens 124 and collimation lens 126 are configured to focus the light so that the light is turned into parallel light.

A reflector 128 may be installed at the incidence surface 122in of the rod lens 122. The reflector 128 is configured to reflect light which is not incident on the incidence surface 122in of the rod lens 122, from the light emitted from lamp 116 and reflected by oval shape reflection mirror 118. Light reflected by reflector 128 is directed back toward the oval shape reflection mirror 118 and reflected again by the oval shape reflection mirror 118 to fall incident on the incident surface 122in of the rod lens 122.

Referring to FIG. 1, an uneven distribution of light is formed at the incident surface 122in positioned at the second focus position of the oval shape reflection mirror 118 and an even distribution of the light is formed at the emitting surface 122out of the rod lens 122. If a ratio of the second focal distance and the first focal distance (e.g., ratio of the focal distance) is above a reference value, a size of the spot of the light beam received at the second focus position of the oval shape reflection mirror 118 (that is, the size of the light beam spot at incident surface 122in of rod lens 122) is increased. When the size of the light beam spot exceeds the area of the incident surface of rod lens 122, a loss of light into the lens 122 occurs. That is, the amount of light which does not fall on incident surface 122in of lens 122 produces a proportional decrease in the amount of light exiting lens 122 from surface 122out.

On the contrary, if the ratio of the focal distance of the oval shape reflection mirror 118 is below a reference value, the size of light beam spot at the second focus position is decreased, and thus the amount of light incident onto the rod lens 122 is increased. Also, the incidence angle of the rod lens 122 is increased and the amount of the light that passes through focus lens 124 and collimation lens 126 disposed behind the rod lens 122 is decreased. As a result, the amount of the light that reaches the wafer 106 is also decreased.

In accordance with one embodiment, the amount of light that reaches wafer 106 may be increased by adjusting the ratio of the focal distance of the oval shape reflection mirror 118 and/or the size of lamp 116. Taking this approach, however, may reduce the flexibility of the design of illumination optic system 102.

In accordance with another embodiment, the structure of the reflector 128 installed at the incidence surface 122in of the rod lens 128 may be modified to allow a greater amount of light to enter rod lens 122. This modification may also allow for increased flexibility of design of illumination optic system 102.

Figure 2:
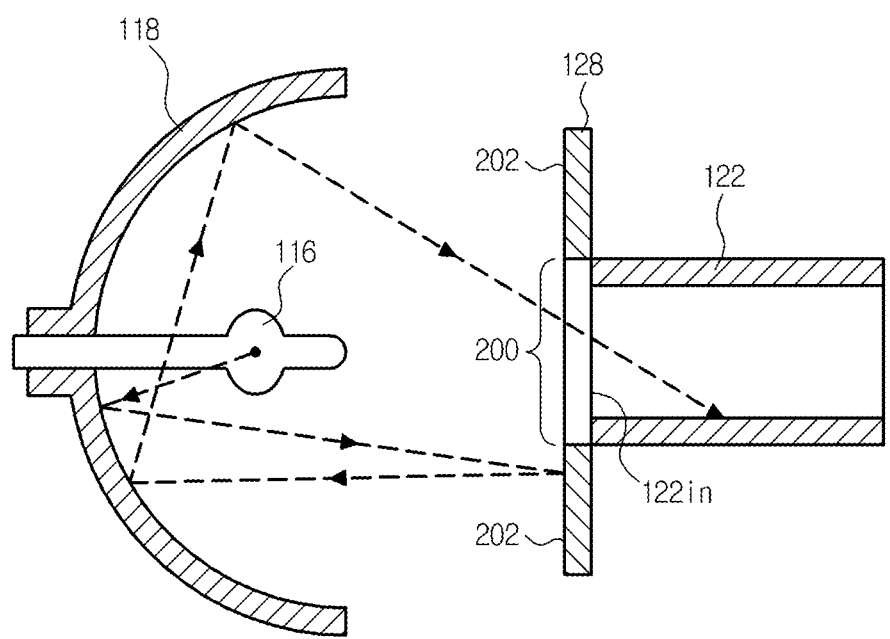
FIG. 2 shows an example of one type of reflector.

FIG. 2 shows a coupling status and operation of the reflector shown in FIG. 1. As shown in FIG. 2, the reflector 128 includes a reflection surface 202 configured to reflect light from light source 116 and mirror 118 which is not incident on the incidence surface 122in of the rod lens 122. The light reflected from surface 202 travels back to oval shape reflection mirror 118. A light guide hole 200 in reflector 128 allows light to pass onto the incidence surface 122in of the rod lens 122.

More specifically, the reflector 128 reflects light that is diverted away from the incidence surface 122in of the rod lens 122 toward the oval shape reflection mirror 118. This light is reflected again by the oval shape reflection mirror 118 to thereby enable the entire light or a portion of the light reflected again by the oval shape reflection mirror 118 to be incident onto the incidence surface 122in of the rod lens 122.

By reflecting the light which is not incident onto the incidence surface 122in of the rod lens 122 toward the oval shape reflection mirror 118, the chance of light to be incident onto the incidence surface 122in of the rod lens 122 is increased, thereby increasing the margin of decreasing the loss of the light.

Figure 3:
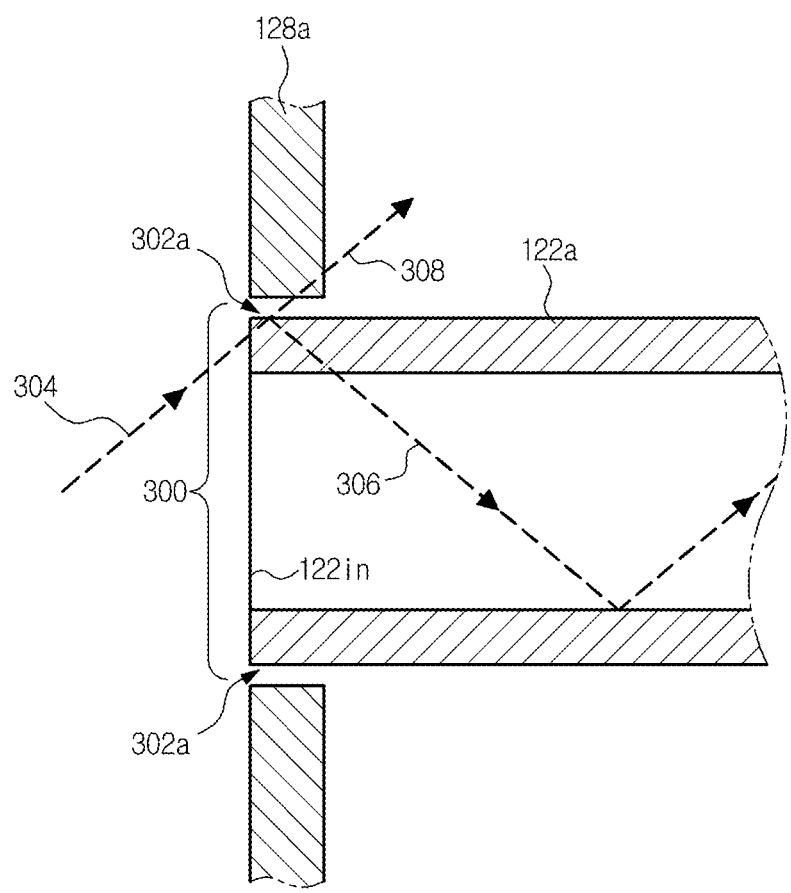
FIG. 3 shows a first embodiment of a reflector.

FIG. 3 is a drawing showing a first embodiment of a reflector 128*a* that may further reduce the loss of light into lens 122 and thus which is used to illuminate wafer 106. As shown, the incidence surface 122in of a rod lens 122*a* is inserted into a light guide hole 300 of a reflector 128*a* by coupling the reflector 128*a* to the rod lens 122. Also, in this embodiment, a space 302*a*, that is, a gap, is formed in between the rod lens 122*a* and the reflector 128*a*.

More specifically, as shown in FIG. 3, the rod lens 122*a* is inserted into the light guide hole 300 of the reflector 128*a* so as to leave a space 302*a* between the rod lens 122*a* and reflector 128*a*. The space 302*a* may be filled with a material different from the material from which the lens 122 is made, or may be filled with air. This space allows incident light 304 that would not have passed through lens 122*s* to pass into lens 122*a*.

In accordance with one embodiment, the space 302*a* between rod lens 122*a* and reflector 128*a* has a distance less than about 100 micrometers, and preferably, in the range of tens of micrometers. In other embodiments, this distance may be different. For example, the distance may be selected to allow lens section 122*a* to produce an internal reflection of light beam 304 at a specific angle through the core of the lens.

In accordance with another embodiment, a second optical element may be placed behind reflector 128 to reflect the un-reflected portion 308 of beam 304 into the lens. This second optical element may be another lens, a mirror, prism, or other type of reflective surface or coating.

Additionally, or alternatively, the difference in index of refraction of the medium in space 302 and the index of refraction of lens 122*a* may produce the reflection of portion 306 of beam 304 into the core portion of lens 122*a*.

In contrast to FIG. 3, if the rod lens 122*a* and the reflector 128*a* are installed in contact with each other, space 302 is not formed in between the rod lens 122*a* and the reflector 128*a*. As a result, a portion 306 of incident light 304 is not directed into rod lens 122*a* and thus a greater amount of lost light may be realized.

Figure 4:
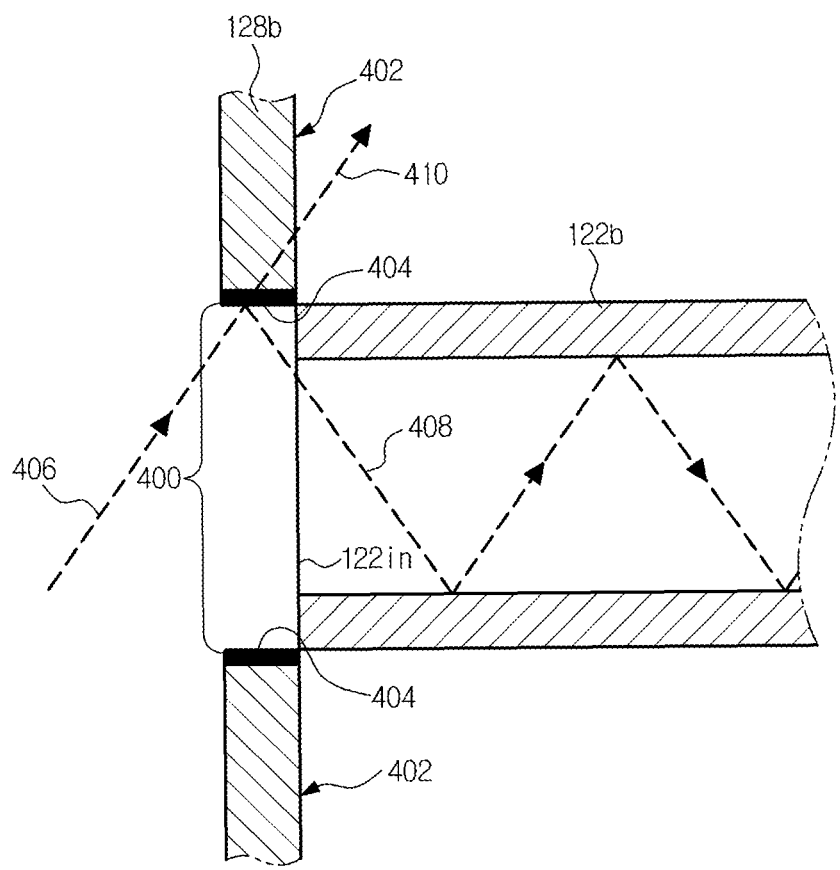
FIG. 4 shows a second embodiment of a reflector.

FIG. 4 shows a second embodiment of a reflector. In this embodiment, a rod lens 122*b* and a reflector 128*b* are disposed in a way that the reflector 128*b* is positioned ahead of the incident surface 122in of the rod lens 122*b* in the light axis. That is, the reflector 128*b* is disposed at a position closer to lamp 116 (which is the light source) than the incident surface 122in of the rod lens 122*b*. Also, the inner surface of a light guide hole 400 of the reflector 128*b* may be coated with reflection material to form a reflection coating surface 404.

With this structure, light 406 outside an angular range reaching the incident surface 122in of the rod lens 122*b* is more likely to be reflected by the reflection coating surface 404 of the reflector 128*b* onto the rod lens 122*b*. The reflected light is illustratively shown by beam 408 in FIG. 4. By comparison, if the reflection coating surface 404 of the reflector 128*b* is not present, the light 406 would be entirely diverted away from the incidence surface 122in of the rod lens 122*b*, for example, along the path shown by dotted arrow 410. As a result, less light would pass through the lens and onto the wafer.

In a variation of the embodiment of FIG. 4, a gap may be formed between coating 404 and lens 122*b*. In this embodiment, reflector 128*b* may be placed ahead of lens 122*b* or may be even with the incident surface of lens 122*b*. Thus, both the coating 404 and the gap may serve to reflect light into the lens in this variation.

Figure 5:
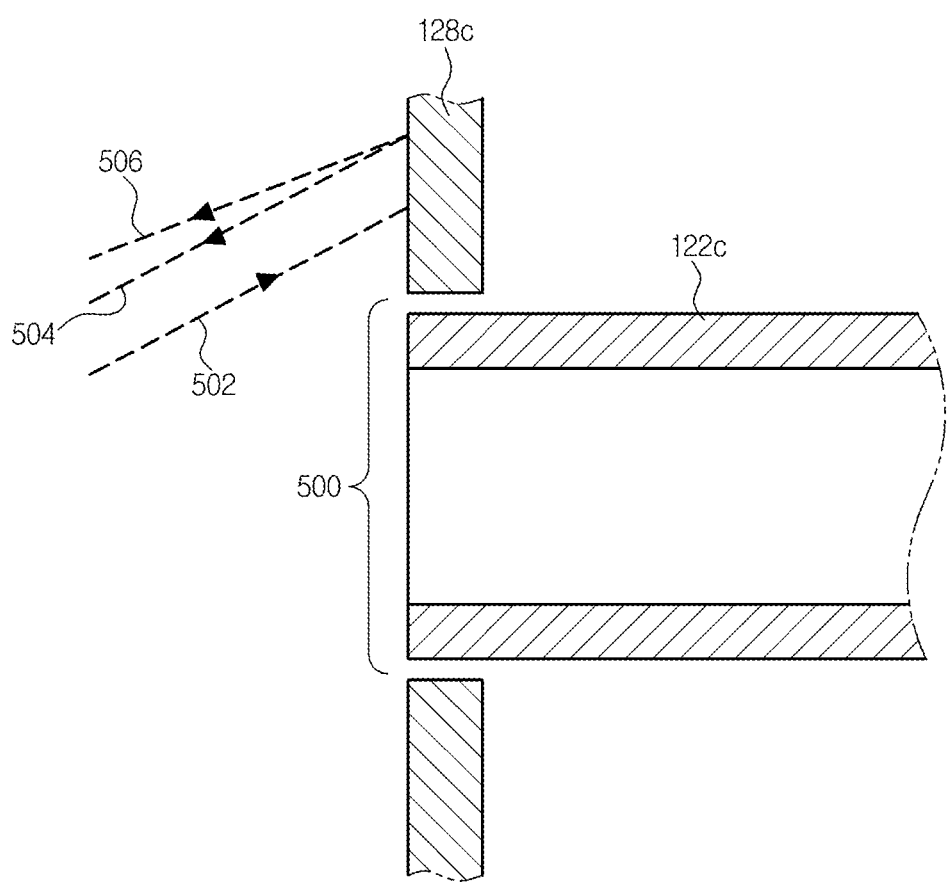
FIG. 5 shows a third embodiment of a reflector.

FIG. 5 shows a third embodiment of a reflector 128*c* which includes a retro-reflector or a retro-reflector array. In this retro-reflector or array, the incident angle and the reflection angle of light may be the same as shown by light beams 502 and 504. Thus, in this embodiment, light 502 which is not incident onto a rod lens 122*c* reflected in a reverse direction back towards oval shape reflection mirror 118. As a result, the amount of light passing into rod lens 122 is increased when compared, for example, to a case of diffused reflection. This may, in turn, may lead to a further reduction in the loss of the light.

Furthermore, the reflection angle of the retro-reflector 128c may be set, changed or adjusted to a desired angle or range of angles to allow for light to be reflected at a variety of angles (e.g., as shown by beams 504 and 506) from the oval shape reflection mirror 118 back toward the lens. Thus, allows for light which is reflected along paths that do not precisely correspond to the incidence angle of the lens to still pass into the lens.

In accordance with one or more of the aforementioned embodiments, light which lies in a certain wavelength band (e.g., in the range of 200 nm and 500 nm) may be reflected into the lens. In one embodiment, this wavelength band may include wavelengths greater than wavelengths of light reflected by a mirror-type reflector.

Also, in accordance with one or more embodiments, a greater amount of light may pass into the lens, thereby reducing loss of light.

Also, one or more embodiments described herein may be less costly to manufacture compared with mirror-type or other arrangement, because no trade-off exists between the shape of reflector and the amount light to be reflected as is the case with other types of mirror reflectors.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. An illumination optic system, comprising:
a light source;
a convex reflection mirror configured to have the light source positioned at a first focus, and allow light radiated from the light source to be reflected so that the reflected light is focused on a second focus;
a lens configured to have an incidence surface thereof positioned on the second focus; and
a reflector provided with a reflection surface configured to reflect light not incident onto the lens toward the convex reflection mirror, the reflector having a light guide hole configured to guide light to the incidence surface of the lens, an inner surface of the light guide hole of the reflector being coated with a reflection material to form a reflection coating surface.

2. The illumination optic system of claim 1, wherein:
the incidence surface of the lens is inserted into the light guide hole so that a gap is between the incidence surface of the lens and the light guide hole of the reflector.

3. The illumination optic system of claim 2, wherein:
the light guide hole has a diameter larger than a diameter of the incidence surface of the lens so as to provide the gap.

4. The illumination optic system of claim 1, wherein:
the reflector and the lens are disposed so that the reflection surface of the reflector is positioned ahead of the incidence surface of the lens in a light axis.

5. The illumination optic system of claim 1, wherein:
the reflector and the lens are disposed so that a rear surface of the reflector is substantially coplanar with the incidence surface of the lens.

6. The illumination optic system of claim 1, wherein:
the reflector is at least one of a mirror, a retro-reflector and a retro-reflector array.

7. The illumination optic system of claim 1, wherein:
the lens is one of a rod lens and a fly-eye lens.

8. An illumination optic system, comprising:
a light source;
a first reflector configured to reflect light from the light source;
a lens in front of the light source and first reflector;
a second reflector adjacent the lens, and
a third reflector adjacent the lens, the second reflector configured to reflect light toward the first reflector, the first reflector configured to reflect light reflected from the second reflector towards the lens, and the third reflector configured to reflect light from the light source and first reflector into the lens.

9. The system of claim 8, wherein the third reflector is a reflective coating.

10. The system of claim 8, wherein the third reflector is coupled to a surface of the second reflector that faces a direction that crosses a central axis of the lens.

11. The system of claim 8, wherein
the second reflector includes a hole, and
the third reflector overlaps the hole in the second reflector.

12. The system of claim 8, wherein
an incident surface of the lens is in a first plane, and
a surface of the second reflector is in a second plane different from the first plane.

13. The system of claim 8, wherein the third reflector contacts the second reflector and the lens.

14. The system of claim 8, wherein the third reflector does not overlap an incident surface of the lens.

* * * * *